United States Patent [19]

Heck

[11] 4,128,554

[45] Dec. 5, 1978

[54] PROCESS FOR THE PREPARATION OF CARBOXYLIC ACID AMIDES FROM ORGANIC HALIDES

[75] Inventor: Richard F. Heck, Wilmington, Del.

[73] Assignee: University of Delaware, Newark, Del.

[21] Appl. No.: 776,289

[22] Filed: Mar. 10, 1977

Related U.S. Application Data

[60] Continuation-in-part of Ser. No. 649,487, Jan. 15, 1976, abandoned, which is a division of Ser. No. 468,762, May 10, 1974, Pat. No. 3,988,358.

[51] Int. Cl.$^2$ ................. C07D 213/56; C07C 103/75
[52] U.S. Cl. .............................. 546/317; 260/326.5 E; 260/558 R; 260/558 D; 260/558 P; 260/561 N; 260/332.2 C; 546/193; 546/281; 546/316; 546/284; 546/205; 546/203; 546/226; 546/245; 542/438

[58] Field of Search ............ 260/295.5 A, 558 R, 260/561 N, 558 D, 558 P, 332.2 C

[56] References Cited

U.S. PATENT DOCUMENTS 3,733,354  5/1973  Cassar et al. .................. 260/515 R

OTHER PUBLICATIONS

Falbe, Carbon Monoxide in Organic Synthesis, pp. 108–112 & 118–120, Springer–Verlag pub. 1970.
Heck et al., J. Am. Chem. Soc., vol. 85 (18), pp. 2779–2782, Sep. 20, 1963.

*Primary Examiner*—Alan L. Rotman

[57] ABSTRACT

Carboxylic acid amides are obtained from aryl, heterocyclic, and vinylic halides and substituted derivates thereof, by reacting same with a primary or secondary amine and carbon monoxide, in the presence of a palladium catalyst and if necessry a tertiary amine at about 20°–150° C and from at least a half atmosphere pressure.

4 Claims, No Drawings

PROCESS FOR THE PREPARATION OF CARBOXYLIC ACID AMIDES FROM ORGANIC HALIDES

The Government has rights in this invention pursuant to Grant No. 73-75-GP3442X awarded by the National Science Foundation.

This application is a continuation-in-part of my copending aplication Ser. No. 649,487 filed Jan. 15, 1976 abandoned Mar. 13, 1977, which was a division of my copending application Ser. No. 468,762 filed May 10, 1974, now U.S. Pat. No. 3,988,358.

This invention relates to a catalytic process for the preparation of carboxylic acid amides from organic halides It is known that allylic chlorides can be converted in poor yield into methyl 3-butenoate derivatives with a palladium catalyst, carbon monoxide and methanol (e.g., D. Medema, R. vanHelden and C. F. Kohll, *Inorg. Chem. Acta*, 3, 255 (1969)). Allylic chlorides are also well known to be very reactive halides and to form isolatable complexes with palladium, $\pi$-allylpalladium chloride dimers. This carboxylation reaction is applicable only to the very reactive allylic halides, however.

It is the object of this invention to catalytically produce carboxylic amides in good yields under mild conditions from organic halides other than allylic halides, including those organic halides that have been considered to be unreactive as compared to allylic halides.

In accordance with the present invention, it has been found that carboxylic amides are produced when aryl, heterocyclic, and vinylic halides or substituted derivatives thereof are in contact with carbon monoxide, a primary or secondary amine and in the presence of a palladium catalyst and if necessary a tertiary amine.

The process of this invention appears to depend upon the reactions broadly expressed as follows:

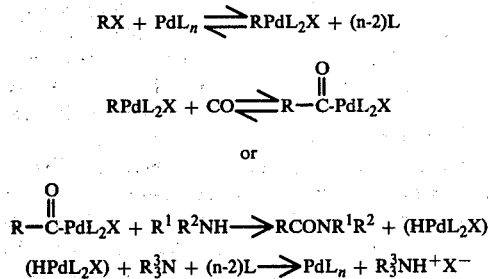

in which R is an aryl, heterocyclic, or vinylic group or substituted derivates thereof with up to about 30 carbonatoms, X is iodide, bromide or chloride, L is a triarylphosphine where n is 2, 3 or 4, $R^1$ is an aryl, alkyl, cycloalkyl, benzylic or a hydrogen group, $R^2$ may be the same as $R^1$ or it may be attached to $R^1$ to form cyclic groups, and $R^3$ is a lower alkyl group, hydrogen, or a cycloalkyl group or two of the $R^3$ groups may be joined to form a ring and the third $R^3$ group would be a lower alkyl, hydrogen or a cycloalkyl group.

The R, $R^1$ and $R^2$ groups as defined above may also have various substituents present such as alkyl and aryl groups, cycloalkyl groups, nitro, cyano, ester, carboxylate, amide, aldehyde and even hydroxylic, amino or substituted amino and halogen groups if these groups are less reactive than the other groups in the reactants which are intended to take part in the reaction. In general the reaction rates are highest when $R^1$ and $R^2$ have less than about 30 carbonatoms.

Examples of organic halides, RX, which will undergo the reaction of this invention are bromobenzene, iodobenzene, p-acetoxyiodobenzene, methyl p-bromobenzoate, p-bromobenzonitrile, o-iodobenzoic acid, p-bromoanisole, m-bromoacetophenone, p-iodophenol, p-chlorobromobenzene, 3-bromopyridine, 2-bromothiophene, benzyl chloride, 2-bromonaphthalene, p-methoxybenzyl chloride, vinyl bromide, bromoacetylene, 1-bromostyrene, 2-bromostyrene, 2-bromopropene, 2-chloropropene, 1-bromocyclohexene, methyl 3-bromoacrylate, 3-iodobenzaldehyde, bromophenanthrene, 3-iodo-3-hexene, 1-bromohexyne, o-bromobenzylamine, m-iodoaniline and 1,2 and 1,4-dibromobenzene.

The coordinating group L is usually triphenylphosphine although other phosphine derivates with up to about 40 carbon atoms such as tri-p-anisylphosphine, trinaphthylphosphine, tri-tolyphosphine, tri-p-tolylphosphine, and tri-p-chlorophenylphosphine may also be used. In some instances with the more reactive RX molecules, particularly iodides, the phosphine derivative may not be necessary at all in which case L becomes a solvent group or a group of one of the other reactants present in the reaction mixture.

Examples of $R^1R^2NH$ which may be used are: ammonia, methylamine, dimethylamine, diethylamine, n-propylamine, n-butylamine, cyclohexylamine, aminothiophene, naphthylamine, aniline, N-methylaniline, p-nitroaniline, p-methoxyaniline, pyrrolidine, piperidine, p-phenylenediamine, methyl glycinate, benzylamine, p-carbomethyoxybenzylamine, ethylenediamine, and abietylamine.

A basic tertiary amine is usually necessary to make the reaction catalytic in palladium. If the amide producing reaction is carried out with a strongly basic primary or secondard amine, it is not necessary to add the tertiary amine, however, but two equivalents of the primary or secondary amine relative to the halide, RX, are then used instead of one. Examples of tertiary amines which can be used are: triethylamine, tri-n-butylamine, triisopropylamine, tetramethylethylenediamine, N-methylpiperidine, N,N-di-cyclohexylethylamine, benzyldiethylamine, dimethylisopropylamine and tri-n-propylamine.

The process of this reaction is carried out at a temperature in the range of 20° C. to about 175° C. with a carbon monoxide pressure of at least one half an atmosphere. The preferred temperatures are about 25°–160° with a pressure of about one to 10 atmospheres of carbon monoxide.

Generally no solvent is necessary for the reaction if the reactant mixture is liquid at the reaction temperature. Solvents such as excess reactant amine, alcohol, tetrahydrofuran, toluene, N-methylpyrrolidone and dimethylformamide may be used, however, with little effect upon the reaction.

The ratios of reactants used is not critical. The organic, halide, RX, may be the limiting reagent in which case a 5–100% or more excess of the primary or secondary amine is used. The reaction may be carried out equally well with equivalent or excess amounts of the organic halides. The tertiary amine is added in amounts equivalent to or in excess of the organic halide.

Catalyst concentrations of from about 0.01 mole percent to about 10 mole percent or more may be used with about 0.1 to 2% being generally preferred. The catalyst may be added as finely divided palladium metal in cases where the RX is an iodide but in other cases palladium (II) salts are preferred such as the dihalides or the diacetate. In the last cases the catalyst usually must be used in conjunction with a triarylphosphine in which cases triarylphosphine palladium complexes are formed under the reaction conditions. While ratios of two phosphines per palladium are generally sufficient higher ratios of up to 30 or more to one are sometimes advantageous in allowing higher steriospecificity to be obtained in the ester producing reaction from cis-vinylic halides.

The following examples illustrate various ramifications of this invention, but the invention is not to be limited thereby.

EXAMPLE 1

A mixture of 17.2 mmoles of bromobenzene, 38 mmoles aniline, 19 mmoles tri-n-butylamine and 0.25 mmole of bromo(bistriphenyphosphine) phenylpalladium was reacted at 100° under one atmosphere of carbon monoxide until gas absorption stopped. After 3.5 hours reaction at 100°, the reaction mixture was cooled and extracted with ether. The extracts were washed with dilute aqueous acid, dried and concentrated. On cooling the solution deposited at 94% yield of colorless crystals of N-phenylbenzamide, m.p. 162.5°–163°.

EXAMPLE 2

Example 1 was carried out with 25 mmoles of benzylamine instead of aniline and here was produced N-benzylbenzamide in 79% yield, m.p. 105°–105.5°.

EXAMPLE 3

Example 1 was carried out with methyl p-bromobenzoate instead of bromobenzene and in 3 hours at 100° there was produced N-phenyl-p-carbomethoxybenzamide in 86% yield, m.p. 192°–193°.

EXAMPLE 4

Example 1 was carried out with p-bromoanisole instead of bromobenzene. After 10 hours reaction time at 100°, there was obtained a 76% yield of p-methoxybenzamide, m.p. 173°–174°.

EXAMPLE 5

Example 1 was carried out with p-bromonitrobenzene instead of bromobenzene. After 3.5 hours at 100° there was formed p-nitrobenzamide in 57% yield, m.p. 211°–212°.

EXAMPLE 6

Example 1 was carried out with 3-bromopyridine instead of bromobenzene and N-phenylnicotinamide was formed in 50% yield, m.p. 118°–119°.

EXAMPLE 7

Example 1 was carried out with 2-bromothiophene rather than bromobenzene and N-phenyl-2-thiophenecarboxamide was formed in 63% yield, m.p. 139°–140°.

EXAMPLE 8

A mixture of 17.2 mmoles of trans-2-bromostyrene, 50 mmoles of pyrrolidine and 0.25 mmole dibromo(bistriphenylphosphine)palladium was heated at 60° for 2.5 hours under one atmosphere of carbon monoxide. Trans-N-Cinnamoylpyrrolidine was isolated from the reaction mixture in 91% yield, m.p. 100°–100.5°.

EXAMPLE 9

Example 8 was carried out with cis-2-bromostyrene in place of the trans isomer and with 25 mmoles of aniline and 19 mmoles of tri-n-butylamine rather than with pyrrolidine. After 4 hours at 60° there was isolated from the reaction mixture an 80% yield of cis-N-phenyl-cinnamamide, m.p. 101°–102°.

EXAMPLE 10

A mixture of 17.2 mmoles cis-3-iodo-3-hexene, 25 mmoles aniline, 19 mmoles tri-n-butylamine and 0.25 mmoles of diiodo(bistrephenylphosphine)palladium was heated and stirred for 1.5 hours at 100° under one atmosphere pressure of carbon monoxide. From the reaction mixture there was isolated a 71% yield of cis-N-phenyl-3-hexene-3-carboxamide, m.p. 96°–97°.

EXAMPLE 11

A reaction was carried out as in Example 10 using E-methyl-3-bromo-2-methylpropenoate instead of cis-3-iodo-3-hexene and dibromo(bistriphenyphosphine)palladium as catalyst. After 2 hours reaction at 100° there was obtained E-N-phenyl-2-carbomethoxy-2-butenamide in 80% yield.

EXAMPLE 12

Example 1 was carried out with 3-bromopyridine instead of bromobenzene and with ammonia instead of aniline in a pressure vessel with 1000 psig. of carbon monoxide at 100°. There was obtained nicotinamide as a product.

EXAMPLE 13

A mixture of 100 mmoles 2-chloropropene, 25 mmoles aniline, 30 mmoles tri-n-butylamine and 0.2 mmoles $PdCl_2(PO_3)_2$ was stirred magnetically in a pressure vessel under 800 psig. of carbon monoxide, at 140° for 12 hours. The gas pressure dropped to about 400 psi. during this time. There was obtained from the reaction mixture a 74% yield of N-phenylmethacrylamide, m.p. 84°–85°. Such high pressures of carbon monoxide are not required for the process of this invention but are used in this example because of the high vapor pressure of the reactants at the temperature used. For example the reaction of 2-chloro-1-octene under the same conditions would require only about one atmosphere or less of carbon monoxide pressure.

As can be seen from the above examples this invention is broadly applicable to a wide variety of organic halides. The products produced by it are valuable compounds used either as chemical intermediates or directly, for example, in the synthetic fiber industry, pharmaceutical or perfumery and flavoring industries. Amides are used in the pharameutical industry. The amide of nicotinic acid for example is a B vitamin and it can be made from 3-bromo-pyridine by the procedure disclosed herein. Furthermore, this invention is generally very simple to use because it often does not require elaborate equipment, high temperatures or high pressures. The catalyst is not only highly effective but also is non-volatile and presents no health hazard to use.

As many apparently widely different embodiments of this invention may be made without departing from the spirit and scope thereof, it is to be understood that this invention is not limited to the specific embodiments thereof except as defined in the appended claims.

I claim:

1. The catalytic process of producing amides from aryl, and heterocyclic halides, with up to about 30 carbon atoms, which comprises reacting said halide with a primary or secondary amine and carbon monoxide in the presence of a palladium-triarylphosphine catalyst at a temperature with the range of from 20° C. to 175° C. and at a pressure of at least about a half an atmosphere and in the presence of a basic tertiary amine if a strongly basic primary or secondary amine is not present in the equivalent or excess of the amount required for the reaction.

2. The process of claim 1 in which the palladium catalyst is a triphenylphosphine complex and is either added as catalyst or such a complex is formed under the reaction conditions by adding the triphenylphosphine and a palladium salt.

3. The process of claim 2 wherein the halides are bromides and the catalyst is a triarylphosphine complex of a palladium halide or a combination of reagents which produces such a complex.

4. The process of claim 3 wherein the bromide is 3-bromopyridine and the product is nictotinamide.

* * * * *